United States Patent
Ezure et al.

(10) Patent No.: US 10,918,590 B2
(45) Date of Patent: Feb. 16, 2021

(54) FAT STEM CELL ATTRACTANT-CONTAINING AGENT FOR IMPROVING SKIN LOOSENESS OR AGING CAUSED BY DERMAL CAVITATION

(71) Applicant: Shiseido Company, Ltd., Tokyo (JP)

(72) Inventors: Tomonobu Ezure, Yokohama (JP); Takahiro Ochiya, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 308 days.

(21) Appl. No.: 15/749,949

(22) PCT Filed: Aug. 4, 2015

(86) PCT No.: PCT/JP2015/072140
§ 371 (c)(1),
(2) Date: Feb. 2, 2018

(87) PCT Pub. No.: WO2017/022091
PCT Pub. Date: Feb. 9, 2017

(65) Prior Publication Data
US 2018/0200179 A1    Jul. 19, 2018

(51) Int. Cl.
*A61K 8/9789* (2017.01)
*A61Q 19/08* (2006.01)
*A61Q 19/00* (2006.01)
*A61K 8/96* (2006.01)
*A61K 36/236* (2006.01)

(52) U.S. Cl.
CPC ............ *A61K 8/9789* (2017.08); *A61K 8/96* (2013.01); *A61Q 19/00* (2013.01); *A61Q 19/08* (2013.01); *A61K 36/236* (2013.01)

(58) Field of Classification Search
CPC .......... A61K 8/96; A61K 8/9789; A61K 8/97; A61K 36/236; A61K 36/53; A61Q 19/00; A61Q 19/08; A61P 17/00; A61P 19/08; A61P 43/00
See application file for complete search history.

(56) References Cited

U.S. PATENT DOCUMENTS

| | | |
|---|---|---|
| 2002/0048594 A1 | 4/2002 | Breton et al. |
| 2004/0121031 A1 | 6/2004 | Majeed et al. |
| 2004/0202638 A1 | 10/2004 | Takada et al. |
| 2011/0081429 A1 | 4/2011 | Aoki et al. |
| 2012/0276044 A1 | 11/2012 | Ra et al. |
| 2014/0004210 A1 | 1/2014 | Iino et al. |

FOREIGN PATENT DOCUMENTS

| | | |
|---|---|---|
| JP | 11-263718 A | 9/1999 |
| JP | 2003-137767 A | 5/2003 |
| JP | 2006-143671 A | 6/2006 |
| JP | 2007-330178 A | 12/2007 |
| JP | 2009-256270 A | 11/2009 |
| JP | 2010-077130 A | 4/2010 |
| JP | 2013-507956 A | 3/2013 |
| JP | 2013-147479 A | 8/2013 |
| RU | 2642672 C2 | 1/2018 |

OTHER PUBLICATIONS

Kim et al., "Antiwrinkle effect of adipose-derived stem cell: Activation of dermal fibroblast by secretory factors," Journal of Dermatological Science, 2009, 53(2):96-102, with English abstract on first page.
Kusumoto, Kenji, "Mitame no Anti Aging Update 7: Various Injection Therapies against Aging Changes on Outer body: in Main Skin Improvement, Wrinkle Therapy and Hair Growth," Anti-Aging Medicine, Japanese Society of Anti-Aging Medicine Zasshi, 2014, 10(6):890-895, with English summary on first page.
Yamaba, Hiroyuki, "Research of skin tension around the eyes," Fragrance Journal, 2008, 36(11):33-38, with English abstract on first page.
Homepage of Rohto Pharmaceutical Co., Ltd., "Discovery of a material that promotes the ability to proliferate and proliferate stem cells derived from fat," 2015, retrieved from https://www.rohto.co.jp/news/release/2015/0616_02.
Alexeev et al., "Human adipose-derived stem cell transplantation as a potential therapy for collagen VI-related congenital muscular dystrophy," Stem Cell Research & Therapy, 2014, 5:21, 17 pages.
Anti-aging medicine-Japanese Society of Anti-aging Medicine Zasshi, 2014, 10(6):890-894, English abstract.
Ezure et al., "Sagging of the cheek is related to skin elasticity, fat mass and mimetic muscle function," Skin Research and Technology, 2009, 15:299-305.
Festa et al., "Adipocyte Lineage Cells Contribute to the Skin Stem Cell Niche to Drive Hair Cycling," Cell, Sep. 2, 2011, 146:761-771.
Fragrance Journal, 2008, 36(11):33-38, partial English translation.
Kim et al., "Current applications of adipose-derived stem cells and their future perspectives," World Journal of Stem Cells, Jan. 26, 2014, 6(1):65-68.
Kim et al., "Wound healing effect of adipose-derived stem cells: A critical role of secretory factors on human dermal fibroblasts," Journal of Dermatological Science, 2007, 48:15-24.
Kroeze et al., "Chemokine-Mediated Migration of Skin-Derived Stem Cells: Predominant Role for CCL5/Rantes," Journal of Investigative Dermatology, 2009, 129:1569-1581.

*Primary Examiner* — Aaron J Kosar
(74) *Attorney, Agent, or Firm* — Foley & Lardner LLP

(57) ABSTRACT

The purpose of the present invention is to provide an agent for improving skin looseness or aging caused by dermal cavitation. By attracting fat stem cells into cavities in the dermis, dermal fibroblasts around the cavities can be activated and thus dermal cavitation can be ameliorated. As the results of a screening for fat stem cell attractants, it was found that rosemary extract and licorice extract are capable of attracting fat stem cells and, therefore, can improve skin looseness or aging caused by dermal cavitation.

11 Claims, 4 Drawing Sheets
Specification includes a Sequence Listing.

(A)

Absence of adipose stem cells    Presence of adipose stem cells (B)

SEQUENCE LISTING

<160> NUMBER OF SEQ ID NOS: 4

<210> SEQ ID NO 1
<211> LENGTH: 20

```
<212> TYPE: DNA
<213> ORGANISM: Artificial Sequence
<220> FEATURE:
<223> OTHER INFORMATION: Primer

<400> SEQUENCE: 1
agcaggcaaa cctggtgaac                                          20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aacctctctc gcctcttgct                                          20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
acggtaacgc aggtgtccta                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ccgctttcac ggtctgtatt                                          20
```

FAT STEM CELL ATTRACTANT-CONTAINING AGENT FOR IMPROVING SKIN LOOSENESS OR AGING CAUSED BY DERMAL CAVITATION

CROSS-REFERENCE TO RELATED APPLICATIONS

This application is a National Stage application of PCT/JP2015/072140, filed Aug. 4, 2015.

TECHNICAL FIELD

The present invention relates to an agent for improving skin sagging or aging caused by dermal cavitation, which comprises an adipose stem cell attractant. More specifically, licorice extract and/or rosemary extract are used as the adipose stem cell attractant.

BACKGROUND ART

In the field of regenerative medicine that is focused on new regeneration of tissues, efforts are being made to exploit various types of stem cells for the purpose of restoring lost tissue functions. Regenerative medicine has come to be implemented not only in the field of medical treatment but also in the field of cosmetics, such as hair restoration and skin regeneration.

Stem cells are cells that have the ability to auto-replicate and differentiate. The known types of stem cells include stem cells, such as embryonic stem cells (ES cells), that have totipotency, allowing them to differentiate into all of the cell types that form an individual, as well as somatic stem cells (hematopoietic stem cells or mesenchymal stem cells) that are not totipotent but have pluripotency, allowing them to differentiate into multiple cell lines.

However, embryonic stem cells can only be obtained from embryos in the initial stage of development, and in consideration of risk to the mother's body during harvesting, as well as ethical considerations, they cannot be easily utilized in research and clinical settings and are also difficult to use in the cosmetic field. While research on the use of somatic stem cells is being conducted in the cosmetic field, because they have extremely low abundance and are difficult to isolate, problems have been faced when attempting to culture them in mass while maintaining their ability to auto-replicate and differentiate.

Although various types of stem cells exist, adipose stem cells isolated from adipose tissue are known to have migratory ability (PTL 1: JP 2013-507958) and the ability to differentiate into different types of cell lines, and these are considered promising for application in many forms of regeneration therapy (NPL 1: World J Stem Cells 2014 Jan. 26; 6(1): 65-68). As an example of application in regeneration therapy, adipose stem cells is demonstrated to contribute to regeneration of hair follicles by functioning as skin niche cells that regulate skin stem cell activity (NPL 2: Cell, (2011) 146, 761-771). In addition, it has been shown that subdermal transplantation of adipose stem cells can accelerate skin wound healing (NPL 3: Journal of Dermatological Science (2007) 48, 15-24). Moreover, it has been disclosed that proliferation of dermal fibroblasts is promoted by contact between adipose stem cells and dermal fibroblasts, the proliferation is known to be useful for wound healing and skin regeneration (NPL 4: Journal of Dermatological Science (2007) 48, 15-24). Adipose stem cell transplant tests have shown a therapeutic effect for congenital muscular dystrophy targeting type 6 collagen, and adipose stem cells are also known to be useful for muscle regeneration(NPL 5: Stem Cell Research & Therapy 2014, 5; 21).

Skin sagging and wrinkle formed on face are a major topic of interest in the cosmetic field. Sagging, in particular, is generally seen near the chin and cheek regions of the faceline. The causes of sagging include reduced function of facial expression muscles, loss of elasticity of the skin supporting the facial expression muscles, and increased subcutaneous fat (NPL 6: Skin Research and Technology, 2009; 15; 299-305). In order to improve sagging effectively, it is thought necessary to identify the causes and devise a corresponding plan of improvement. For example, when the major cause of sagging is reduced function of facial expression muscles, exercising of the facial expression muscles is effective to improve the sagging. When the major cause of sagging is reduced skin elasticity, it is effective to ingest accelerators that promote production of elastic fibers associated with skin elasticity, such as collagen and elastin. When the major cause of sagging is increased subcutaneous fat, exercise and caloric restriction, as well as additives that burn body fat, are effective (PTL 2: Japanese Unexamined Patent Publication No. 2007-330178). It is seldom the case that sagging is due to a single cause, as it is usually due to a combination of causes. Consequently, oral compositions aimed at improving sagging have been disclosed that comprise multiple active ingredients including the following 3 types: two or more mucopolysaccharides, partial collagen decomposition products, and coenzyme Q10 (PTL 3: Japanese Unexamined Patent Publication No. 2006-143671).

CITATION LIST

Patent Literature

[PTL 1] Japanese Patent Public Inspection No. 2013-507958
[PTL 2] Japanese Unexamined Patent Publication No. 2007-330178
[PTL 3] Japanese Unexamined Patent Publication No. 2006-143671

Non-Patent Literature

[NPL 1] World J Stem Cells 2014 Jan. 26; 6(1): 65-68
[NPL 2] Cell, (2011)146, 761-771
[NPL 3] Journal of Dermatological Science (2007) 48, 15-24
[NPL 4] Journal of Dermatological Science (2007) 48, 15-24)
[NPL 5] Stem Cell Research & Therapy 2014, 5; 21)
[NPL 6] Skin Research and Technology, 2009; 15; 299-305)

DISCLOSURE OF THE INVENTION

Problems to be Solved by the Invention

The present invention relates to development of a drug that improves skin sagging.

Means for Solving the Problems

Having conducted avid research on the aging phenomenon of skin, in particular skin sagging, the present inventors found that one of the causes of sagging is dermal cavitation. Upon further avid research on methods of improving sagging by filling in the cavities of the cavitated dermis, it was found that the cavities can be filled in by attracting adipose stem cells. Furthermore, upon screening for cosmetic materials capable of attracting adipose stem cells, it was found that licorice and/or rosemary extract attract adipose stem cells, thereby the present invention has been attained. The present invention thus relates to the following.

[1] An adipose stem cell attractant comprising licorice extract or rosemary extract.

[2] An agent for improving skin sagging or aging caused by dermal cavitation, comprising the adipose stem cell attractant according to item [1].

[3] The agent for improving skin sagging or aging according to item [2], wherein the dermal cavities are filled in with dermal structure under the influence of adipose stem cells attracted in the dermal cavities by the adipose stem cell attractant according to item [1].

[4] The agent for improving skin sagging or aging according to item [3], which includes dermal fibroblasts and interstitial components produced by the dermal fibroblasts, due to the attracted adipose stem cells.

[5] The agent for improving skin sagging or aging according to any one of items [2] to [4], wherein the adipose stem cell attractant according to item [1] permeates through accessory organs.

[6] The agent for improving skin sagging or aging according to any one of items [2] to [5], wherein the adipose stem cell attractant according to item [1] acts on dermal cavities.

[7] A cosmetic method for improvement of skin sagging or aging caused by dermal cavitation, the method comprising a step of applying an adipose stem cell attractant.

[8] The cosmetic method according to item [7], wherein the applied adipose stem cell attractant attracts adipose stem cells in the dermal cavities, and the dermal cavities are filled by dermal structure under the influence of the attracted adipose stem cells.

[9] The cosmetic method according to item [8], wherein the dermal structure includes dermal fibroblasts and interstitial components produced by the dermal fibroblasts.

[10] The cosmetic method according to any one of items [7] to [9], wherein the applied adipose stem cell attractant permeates through accessory organs.

[11] The cosmetic method according to any one of items [7] to [10], wherein the applied adipose stem cell attractant acts in the dermal cavities.

[12] The cosmetic method according to any one of items [7] to [11], wherein the adipose stem cell attractant comprises licorice extract and/or rosemary extract.

[13] A method for ameliorating skin sagging or aging, the method comprising administration of an adipose stem cell attractant to an individual suffering from sagging of skin by dermal cavitation.

[14] The method for ameliorating skin sagging or aging according to item [13], wherein the applied adipose stem cell attractant attracts adipose stem cells in the dermal cavities, and the dermal cavities are filled in with dermal structure under the influence of the attracted adipose stem cells.

[15] The method for ameliorating skin sagging or aging according to item [14], wherein the dermal structure includes dermal fibroblasts and interstitial components produced by the dermal fibroblasts.

[16] The method for ameliorating skin sagging or aging according to any one of items [13] to [15], wherein the adipose stem cell attractant permeates through accessory organs.

[17] The method for ameliorating skin sagging or aging according to any one of items [13] to [16], wherein the adipose stem cell attractant acts on dermal cavities.

[18] The method for ameliorating skin sagging or aging according to any one of items [13] to [17], wherein the adipose stem cell attractant comprises licorice extract and/or rosemary extract.

[19] Use of an adipose stem cell attractant for production of a medicine for improving skin sagging or aging caused by dermal cavitation.

[20] The use according to item [19], wherein the dermal cavities are filled in with dermal structure under the influence of adipose stem cells attracted in the dermal cavities by the adipose stem cell attractant.

[21] The use according to item [20], wherein the dermal structure includes dermal fibroblasts and interstitial components produced by the dermal fibroblasts.

[22] The use according to any one of items [19] to [21], wherein the applied adipose stem cell attractant permeates through accessory organs.

[23] The use according to any one of items [19] to [22], wherein the adipose stem cell attractant acts in the dermal cavities.

[24] The use according to any one of items [19] to [23], wherein the adipose stem cell attractant comprises licorice extract and/or rosemary extract.

[25] An adipose stem cell attractant comprising licorice extract or rosemary extract.

[26] A composition for improving symptoms that are the therapeutic target with mesenchymal stem cells, the composition comprising an adipose stem cell attractant according to item [25].

[27] An adipose stem cell attractant, wherein the improvement of symptoms that are therapeutic target of with the mesenchymal stem cells is hair growth acceleration, wound healing, skin regeneration, muscle regeneration, soft tissue regeneration, bone regeneration, myocardial regeneration or nerve regeneration.

[28] A method of attracting adipose stem cells, the method comprising administration of a licorice extract or rosemary extract to an individual in need of adipose stem cell attraction.

[29] A method of treating or improving symptoms that are the target of treatment with mesenchymal stem cells, by the attracting method according to item [28].

[30] The method according to item [29], wherein the purpose of the improvement of symptoms that are the therapeutic target with the mesenchymal stem cells is hair growth acceleration, wound healing, skin regeneration, muscle regeneration, soft tissue regeneration, bone regeneration, myocardial regeneration or nerve regeneration.

[30] A cosmetic method comprising adipose stem cell attraction by applying a cosmetic comprising a licorice extract or rosemary extract.

[31] The cosmetic method according to item [30], wherein the purpose is hair growth acceleration, wound healing or skin regeneration.

[32] Use of a licorice extract or rosemary extract for production of a medicine for adipose stem cell attraction.

[33] The use according to [32] above, for treatment of a disease and symptoms that are the target of treatment with mesenchymal stem cells, by attraction of adipose stem cells.

[34] The use according to [33] above, wherein the purpose of the improvement of symptoms that are the target of treatment with the mesenchymal stem cells is hair growth acceleration, wound healing, skin regeneration, muscle regeneration, soft tissue regeneration, bone regeneration, myocardial regeneration or nerve regeneration.

[35] An agent for improving skin sagging or aging caused by dermal cavitation, comprising an adipose stem cell attractant.

[36] The agent for improving skin sagging or aging according to item [35], wherein the dermal cavities are filled in with dermal structure under the influence of adipose stem cells attracted in the dermal cavities by an adipose stem cell attractant.

[37] The agent for improving skin sagging or aging according to item [36], wherein the dermal structure includes dermal fibroblasts and interstitial components produced by the dermal fibroblasts.

[38] The agent for improving skin sagging or aging according to item [36] or [37], wherein the adipose stem cell attractant permeates through accessory organs.

[39] The agent for improving skin sagging or aging according to any one of items [35] to [38], wherein the adipose stem cell attractant acts on dermal cavities.

[40] The agent for improving skin sagging or aging according to any one of items [35] to [39] above, wherein the adipose stem cell attractant comprises licorice extract and/or rosemary extract.

[41] An agent for improving skin sagging or aging caused by dermal cavitation comprising an adipose stem cell attractant, wherein the adipose stem cell attractant attracts adipose stem cells in dermal cavities, and the dermal cavities are filled by dermal structure under the influence of the attracted adipose stem cells.

Effect of the Invention

The adipose stem cell attractant used in the agent for improving skin sagging or aging according to the present invention acts by attracting adipose stem cells in dermal cavities. Adipose stem cells can promote proliferation of dermal fibroblasts and production of interstitial components by dermal fibroblasts, thereby filling in the dermal cavities that are a cause of skin sagging or aging.

BEST MODE FOR CARRYING OUT THE INVENTION

Figure 1:
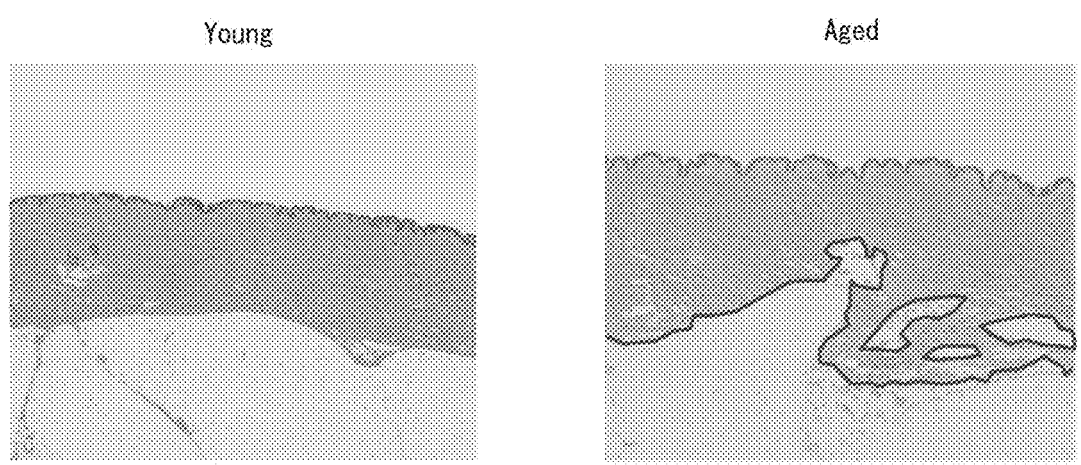
FIG. 1 is a pair of stained photographs of the dermis layers of skin tissue specimens taken from skin of a young individual and an aged individual. In the aged individual, dermal cavities can be seen to have formed by rising of subcutaneous tissue.

The present invention relates to an agent for improving skin sagging or aging caused by dermal cavitation, which comprises an adipose stem cell attractant. An "adipose stem cell attractant" is a drug that can attract adipose stem cells. According to a preferred mode, the adipose stem cell attractant can attract adipose stem cells into dermal cavities of skin.

Adipose stem cells, also known as adipose tissue-derived mesenchymal stem cells, are a type of mesenchymal stem cell present in adipose tissue. Adipose stem cells are known to have migratory ability (NPL 1 and PTL 1), being able to move through adipose tissue. Adipose stem cells are characterized by expression of CD90 marker and CD105 marker, but are not intended to be restricted to cells expressing these markers. Adipose stem cells express various cell growth factors or intercellular signaling factors, which can promote proliferation of dermal fibroblasts and production of interstitial components, in particular collagen, from dermal fibroblasts. Therefore, surrounding dermal fibroblasts are activated by attraction of adipose stem cells.

The adipose stem cell attractant may be any substance that can attract adipose stem cells. The adipose stem cell attractant may also be a drug that can accelerate migration and proliferation of adipose stem cells, in addition to its attracting effect. The adipose stem cell attractant may be any of biological factors, such as a chemokines or cytokines, or polypeptide or proteins, or it may be a cosmetic material or pharmaceutical material such as a low molecular compound, high molecular compound or extract. SDF1α is a substance that can be used as an adipose stem cell attractant. Cosmetic materials are preferred from the viewpoint of use for cosmetic purposes, and plant extracts such as licorice extract or rosemary extract are examples. The adipose stem cell attractant may be used as a single extract alone, or as a mixture of two or more, and it may also be used in combination with known adipose stem cell attractants.

The extraction solvent used to obtain the plant extract may include water or an organic solvent, for example an aliphatic monohydric alcohol such as methanol, ethanol or propanol; an aliphatic polyhydric alcohol such as glycerin, propylene glycol or 1,3-butylene glycol; a ketone such as acetone; diethyl ether, dioxane, acetonitrile, an ester such as ethyl acetate ester; an aromatic such as xylene, benzene or toluene; alkyl halide such as chloroform. These extraction solvents may be used alone or in mixtures of two or more. The mixing ratio of extraction solvents that are mixed is not particularly restricted and may be adjusted as appropriate. The extraction solvent is preferably a water-containing extraction solvent, including at least water.

The method of extraction to obtain the plant extract is not particularly restricted, and common extraction methods known in the prior art may be employed. For the extraction, the portion of the plant to be utilized as the extraction starting material may be used directly or dried first. Purification such as filtration, deodorization and decoloration may also be carried out after extraction, as necessary and appropriate. The adipose stem cell attractant or agent for improving skin sagging or aging is added to a final product for use. The concentration of each extract in the final product is not particularly restricted, and for example, for most cases the extract is typically in the range of 0.001 to 10 mass %, preferably in the range of 0.001 to 1 mass % and most preferably in the range of 0.01 to 0.5 mass %, with respect to the composition, from the viewpoint of exhibiting a sufficient adipose stem cell attracting effect.

Rosemary extract is an aromatic extract derived from rosemary (*Rosmarinus officinalis*), an evergreen shrub of the Lamiaceae family that is indigenous to the Mediterranean coast, and the plant roots, leaves, stems, flower, or the entire plant, may be used as starting material. The extraction method used may be any desired method, and for example, rosemary leaves may be subjected to steam distillation or solvent extraction to obtain an extract. The solvent used may be any extraction solvent. Preferably an extract obtained by extraction with 50% (v/v) butylene glycol is used.

Licorice extract is derived from licorice (*Glycyrrhiza glabra* L. or *Glycyrrhiza uralensis* Fisher), a perennial herb of the bean family, and the plant roots, leaves, stems or flowers, or the entire plant, may be used as starting material. Licorice root contains sweetness components such as glycyrrhizin, glucose and sucrose. It is well known that decomposition products of glycyrrhizin bind to harmful products in the liver in vivo, performing a detoxicating function. Licorice extract is preferably obtained using licorice root as the starting material, and the extraction method may be any desired method such as steam distillation or solvent extraction. The solvent used may be any extraction solvent. Preferably an extract obtained by extraction with 50% (v/v) butylene glycol is used. The licorice extract may be licorice extract powder or licorice flavonoid (oil-soluble licorice extract) conforming to cosmetic compounding ingredient standards, or licorice raw extract or licorice extract listed in the Japanese Pharmacopoeia.

Attraction of adipose stem cells can be confirmed either in vitro or in vivo. For an in vitro experiment, the attracting effect of an adipose stem cell attractant can be determined by culturing adipose stem cells in culture media having different concentrations of adipose stem cell attractant and detecting migration. For in vivo confirmation, the presence or absence of attraction can be examined by calculating the number and proportion of adipose stem cells in the tissue specimen after administration of the adipose stem cell attractant.

Figure 2:
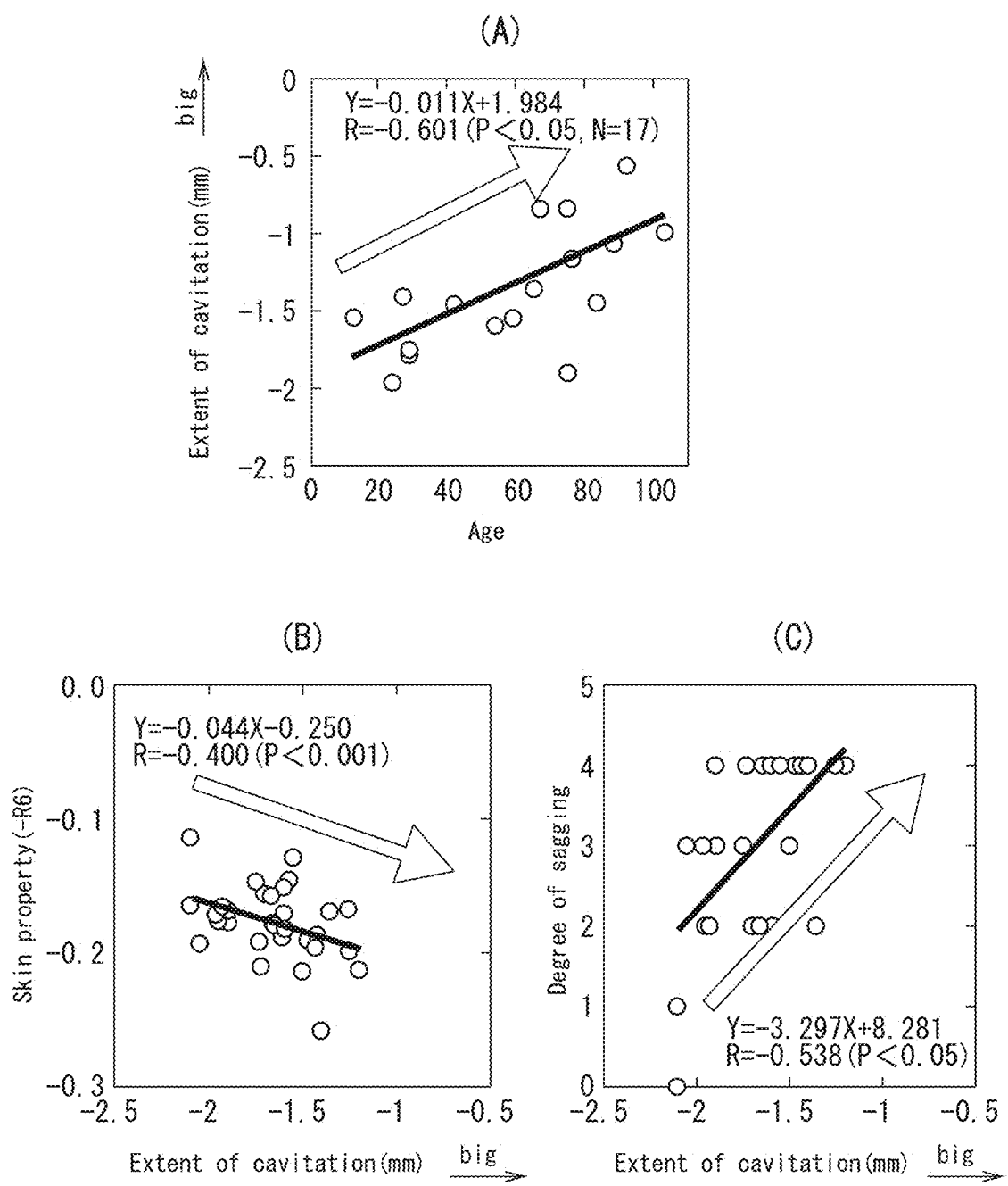
FIG. 2A is a graph showing the relationship between degree of cavitation and age.
FIG. 2B is a graph showing the relationship between skin property and degree of cavitation.
FIG. 2C is a graph showing the relationship between degree of sagging and degree of cavitation.

Dermal cavities are cavities formed by partial rising of subcutaneous tissue on the dermis layer side, by aging or by some other cause (FIG. 1). The sizes of dermal cavities range from 10 μm to 1000 μm in diameter with approximately spherical shapes, though the shapes are not consistent. Because the dermal cavity interiors are filled by subcutaneous tissue, they may be referred to as "dermal hollow". The cellular components and interstitial components in the dermis layer are not found in dermal cavities, and therefore the skin loses its elasticity and exhibits sagging, which result in skin aging. The presence of dermal cavities also results in partially thinning of the dermis, another cause of skin sagging and aging. Actual studies have demonstrated that a higher degree of dermal cavitation leads to lower skin elasticity and a higher degree of apparent sagging (FIGS. 2B and C).

The extent of dermal cavities can be measured by integrating the dermal thickness, i.e. the thickness from the boundary with the epidermis to the boundary with the subcutaneous tissue, in a fixed-length skin in cross-section. When dermal cavities are present, the subcutaneous tissue rises to the dermis layer side, and the thickness of the dermis decreases. Since the thickness of the epidermis is normally constant and somewhat thinner compared to the dermis, it can be calculated by simply estimating the thickness from the skin surface to the subcutaneous tissue. Because the extent of dermal cavities is correlated with elasticity of skin (FIG. 2B), an index of skin elasticity such as the Uv/Ue value may be measured instead, using a device that measures skin elasticity, such as a Cutometer.

The reference to "under the influence of the adipose stem cells attracted in dermal cavities by an adipose stem cell attractant" means that the attracted adipose stem cells act directly or indirectly. That is, the adipose stem cells attracted in the dermal cavities may indirectly activate dermal fibroblasts that are present in the surrounding region by secretion of various cell activating factors. The activated dermal fibroblasts undergo cell proliferation, and production of interstitial components is increased. The proliferated dermal fibroblasts and the produced interstitial components form a superposed dermal structure, and the dermal cavities become filled by the dermal structure. Moreover, since the adipose stem cells are mesenchymal stem cells, they can differentiate into dermal cells such as fibroblasts, thereby allowing the dermal cavities to be directly improved. Thus the dermal cavities are improved by attraction of adipose stem cells into the dermal cavities.

The dermis is composed mainly of cell components such as fibroblasts, histiocytes, mast cells, plasmocytes and dendritic cells, and interstitial components that fill the regions between the cells. Interstitial components are largely classified as collagen fibers composed of collagen, elastic fibers composed of fibrin and elastin, and the matrix composed mainly of glycoproteins and proteoglycans present between the fibers and cells.

The agent for improving skin sagging or aging according to the invention can be administered to an individual suffering from sagging and/or aging of skin due to dermal cavities. The causes of sagging include reduced function of facial expression muscles, reduced elasticity of skin supporting the facial expression muscles and increased subcutaneous fat, these factors working independently or in concert to cause sagging and visible signs of aging. According to the invention, administration is to an individual suffering from skin sagging. The major cause of the sagging in the individual is preferably reduced elasticity of skin, and especially reduced elasticity of skin due to decreased thickness of the dermis layer resulting from dermal cavities. The extent of dermal cavitation may be measured in order to confirm whether dermal cavities are the main cause of the skin sagging. The agent for improving skin sagging or aging and the cosmetic method of the invention are preferably applied to an individual with a high degree of cavitation. It can be determined that an individual has a high extent of cavitation if the individual has a value exceeding a threshold value established from numerical values for extent of dermal cavitation.

The agent for improving skin sagging or aging of the invention may be administered by any route such as oral or parenteral administration, but the route is preferably transdermal administration from the viewpoint of direct administration to the skin. A transdermally administered adipose stem cell attractant can permeate through the accessory organs such as pores and sweat glands in the skin. Since accessory organs usually extend to the deepest parts of the dermis layer, they are extremely close to dermal cavities when present. Consequently, a transdermally administered adipose stem cell attractant can be delivered into dermal cavities which are the site of action, by permeating through the accessory organs. Moreover, the viscosity, surface tension, hydrophilicity and hydrophobicity of the agent for improving skin sagging or aging may be selected as appropriate in order to promote permeation through accessory organs into dermal cavities as the sites of action. In addition, in order to promote permeation into dermal cavities, high frequency vibration or ultrasound may be applied after application of the agent for improving skin sagging or aging of the invention.

The agent for improving skin sagging or aging according to the invention may also be added to a cosmetic, pharmaceutical or quasi drug. It is preferably added to a cosmetic for the purpose of beautification. The cosmetic to which it is added may be in any dosage form, and may be used in admixture in the form of a liquid, gel, foam, latex, cream, ointment or sheet. The cosmetic, pharmaceutical or quasi drug to which it is added may be applied for various products including formulations for external use, base cosmetics such as cosmetic water, latexes, cream, ointments, lotions, oils or packs, face cleansers or skin rinsers, hair removers, depilatories, aftershave lotions, preshave lotions, shaving cream, makeup cosmetics such as foundations, lipstick, rouge, eye-shadow, eyeliner or mascara, hair cosmetics such as shampoo, rinses, hair treatments, pre-hair treatments, hair dressings, hair-perm agents, hair tonics, hair dyes, hair growth agents or hair tonics, or bath preparations.

According to another aspect, the invention relates to a method of screening agents for improving skin sagging or aging caused by dermal cavitation. The screening method can examine the attracting power of the test substance by culturing adipose stem cells in culture media having different concentrations of a test substance. More specifically, a cell migration test well may be used having a construction provided with one or more flow channels having diameters sufficient for the cultured cells to pass through, and with a cell culturing well placed at the entrance of one flow channel and a test substance-adding well placed at the other. The flow channel may also be replaced with a membrane of fixed pore size. The test substance agents to be used for screening may be any drug agents, and for development of a cosmetic product, test substances may be selected from a cosmetic material library of substances whose safety has already been confirmed.

The liquorice extract or rosemary extract obtained by the screening has adipose stem cell attracting activity, and can be used as an adipose stem cell attracting agent or composition. Adipose stem cells are mesenchymal stem cells that are known to differentiate to various mesenchymal cells, including adipocytes, osteoblasts, chondrocytes, muscle cells and nerve cells (NPL 1). NPL 1 discloses that chondrocytes derived from adipose stem cells can be used for treatment of articular cartilage diseases such as arthrosis deformans, and that osteoblasts derived from adipose stem cells can be applied to sites of bone loss, and by differentiation to cardiac muscle or vascular cells, can contribute to improved cardiac function. In addition, since factors secreted from adipose stem cells promote vascularization, reduce cellular apoptosis and accelerate neural sprouting, applications to regenerative medicine are expected not only directly by differentiation of adipose stem cells to target cells, but also indirectly by using secreted factors. Therefore, an adipose stem cell attracting composition of the invention can be used for treatment or improving symptoms that are the target of treatment with mesenchymal stem cells, and particularly adipose stem cells. Improvement of symptoms that are the target of treatment with mesenchymal stem cells includes hair growth acceleration, wound healing, skin regeneration, muscle regeneration, soft tissue regeneration, bone regeneration, myocardial regeneration and nerve regeneration. Among these, in regard to the relationship between adipose stem cells and hair growth acceleration, NPL 2 has disclosed that they function as skin niche cells that regulate skin stem cell activity, thereby contributing to regeneration of hair follicles, and that hair growth acceleration is possible by attracting adipose stem cells. In regard to the relationship between adipose stem cells and wound healing and/or skin regeneration, NPL 3 has disclosed that contact between adipose stem cells and dermal fibroblasts promotes proliferation of dermal fibroblasts, which is known to be useful for wound healing or skin regeneration. In addition, in regard to the relationship between adipose stem cells and muscle regeneration, NPL 4 has disclosed that adipose stem cell transplant tests have shown a therapeutic effect for congenital muscular dystrophy targeting type 6 collagen, and that adipose stem cells are useful for muscle regeneration as well.

EXAMPLES

Detection of Dermal Cavitation

Skin tissue specimens were obtained from the abdominal regions of young and aged female participants, and were supplied for hematoxylin-eosin staining. The hematoxylin/eosin staining reagent was used in a common measuring method, and the stained tissue was observed under a microscope (FIG. 1). The boundary between the dermal tissue and subcutaneous tissue was smooth in the skin tissue specimen from the young individual, the boundary between the dermal tissue and subcutaneous tissue was irregular in the skin tissue specimen from the aged individual, and portions of the subcutaneous tissue had dermal cavities due to rising.

Measurement of Skin Sagging

A test was conducted with 30 healthy female participants (Japanese) aged 30-50, with standard body types and a body mass index (BMI) of <25. The participants were asked to wash the face and readied in a standard environment. Facial photographs were taken with a digital camera (Nikon D-100; Nikon Corporation, Tokyo, Japan) under standard lighting conditions, while the participant was sitting at a left-right angle of 45°. The gravity of cheek sagging was evaluated according to a previously reported method (Ezure T, Hosoi J, Amano S, Tsuchiya T. Skin Res Technol. 2009 August; 15(3):299-305), based on a 6-grade scale, judging from the photographs.

Observation of Dermal Cavitation

The internal structure of the dermis layer was observed in a noninvasive manner by ultrasound. Measurement was at the same location and with the same posture as by measurement with a Cutometer. A Prosound Alpha 5 (Aloka Co., Ltd., Tokyo, Japan), as a 13 MHz probe, was applied perpendicular to the skin that was covered with a thin-layer of ultrasonic gel, and the skin structure was measured using B mode. The shortest distance from the epidermis to the adipose layer was measured using Image J, and the sign-inverted value (mm) was recorded as the extent of dermal cavitation.

Measurement of Dermal Elasticity

The dermal elasticity was evaluated with a noninvasive skin elasticity meter (Cutometer MPA 580™, Courage & Khazaka, Cologne, Germany), based on measurement of skin deformation and recovery upon suction and release. A large-diameter (6 mm) suction probe was used. The participant was asked to lie down on a bed with the face at a 45° angle, in order to reduce the effect of gravity on dermal elasticity measurement. The measurement point was set at the center of the cheek region. Skin suction was carried out for 2 seconds with a pressure of 400 mbar, followed by a relaxation period of 2 seconds, and the values for Ue (immediate distension of the skin, representing elastic deformation), Uv (viscoelastic creep occurring after the elastic deformation), Uf (final distension at the end of the vacuum period, representing the total extensibility of the skin) and Ur (the immediate retraction of the skin, meaning elastic deformation recovery) were obtained from a skin deformation curve. The value for Uv/Ue (ratio of viscoelastic to elastic distension) was calculated and used as the skin property (Skin Research and Technology 2010; 16: 332-338, Skin Research and Technology 2012; 18: 259-264).

For the extent of cavitation, skin property, age and degree of sagging as determined above, FIG. 2(A) shows the relationship between age and extent of cavitation, FIG. 2(B) shows the relationship between extent of cavitation and skin property, and FIG. 2(C) shows the relationship between extent of cavitation and degree of sagging. The relationship between age and extent of cavitation in FIG. 2A and the relationship between extent of cavitation and skin property in FIG. 2(B) were analyzed by the Pearson test. The relationship between extent of cavitation and degree of sagging in FIG. 2(C) was analyzed by the Spearman test.

Test of Dermal Fibroblast Activation by Adipose Stem Cells

Figure 3:
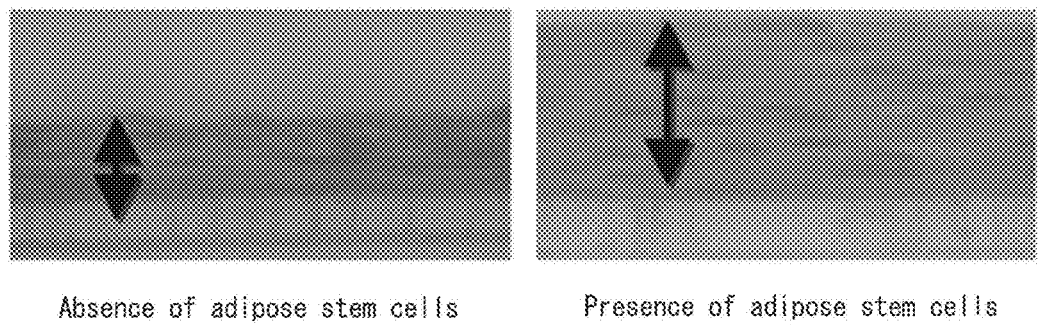
FIG. 3 is a pair of photographs (FIG. 3A) and a graph (FIG. 3B) showing change in cultured dermal fibroblasts in the presence and in the absence of adipose stem cells.
Figure 3:
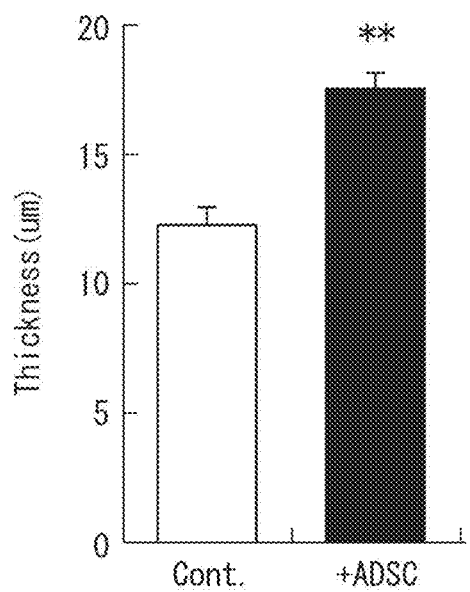

Dermal fibroblasts were purchased from Lonza and cultured in DMEM containing 10% FBS. Adipose stem cells (ADSC) were purchased from Invitrogen and cultured in MessenPro RS medium. The dermal fibroblasts were seeded on the upper layer of a Transwell (Transwell for 6 well plate: Falcon) at $1\times10^4$ cells/well. The ADSCs were treated for 3 hours with 10 µg/mL mitomycin, and then seeded on the lower layer of a Transwell (Transwell for 6 well plate) at $2\times10^5$ cells/well. After 24 hours, the medium was exchanged with DMEM containing 10% FBS, 250 µM ascorbic acid, and co-culturing was started. After 7 days, the upper layer was fixed with paraformaldehyde, HE stained, and observed (FIG. 3A). The thickness of the upper layer was measured, and is shown in FIG. 3B. As a control, fibroblasts alone were cultured without ADSCs. In the presence of ADSCs, the dermal fibroblasts were activated and the thickness of the dermis layer increased (Student's t-test: $P<0.05$).

Figure 4:
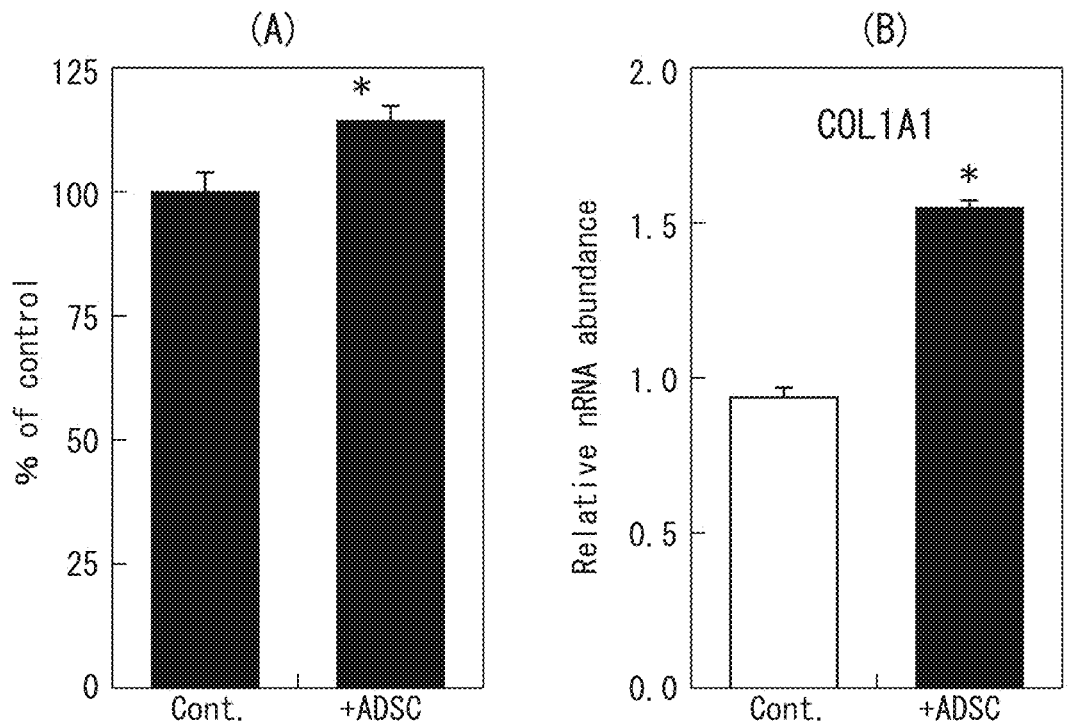
FIG. 4 is a graph showing change in the number of cultured dermal fibroblasts (FIG. 4A) and a graph showing change in collagen production (FIG. 4B), in the presence and in the absence of adipose stem cells.

Dermal fibroblasts were purchased from Lonza and cultured in DMEM containing 10% FBS. Adipose stem cells (ADSC) were purchased from Invitrogen and cultured in MessenPro RS medium. The dermal fibroblasts were seeded on the upper layer of a Transwell (Transwell for 6 well plate: Falcon) at $1\times10^5$ cells/well. The ADSCs were treated for 3 hours with 10 µg/mL mitomycin, and then seeded on the lower layer of a Transwell (Transwell for 6 well plate) at $2\times10^5$ cells/well. After 24 hours, the medium was exchanged with DMEM containing 10% FBS, 250 µM ascorbic acid, and co-culturing was started. After 48 hours, the cells were collected and supplied for RT-PCR and Alamar Blue assay. The RT-PCR was carried out by reverse transcription using a LightCycler Kit (Roche) according to the product manual, and the following primers were used for quantitation (FIG. 4B). For the AlamarBlue assay, AlamarBlue (Bio-Rad Company) was used according to the product manual, and the viable cell count was determined (FIG. 4A). In the presence of ADSCs, the viable cell count increased (Student's t-test: $P<0.05$), while the expression level of collagen (COL1A1) also increased (Student's t-test: $P<0.05$).

TABLE 1

Table 1

| Primer name | Sequence |
|---|---|
| Col1A1 Forward | AGCAGGCAAACCTGGTGAAC (SEQ ID NO 1) |
| Col1A1 Reverse | AACCTCTCTCGCCTCTTGCT (SEQ ID NO 2) |
| 28S rRNA Forward | ACGGTAACGCAGGTGTCCTA (SEQ ID NO 3) |
| 28S rRNA Reverse | CCGCTTTCACGGTCTGTATT (SEQ ID NO 4) |

Adipose Stem Cell Attraction Test

Stem cells derived from fat (Invitrogen (Carlsbad, Calif.)) were cultured in a flask containing MessenPro RS medium (DMEM; GIBCO/BRL (Carlsbad, Calif.)), under moist conditions with 37° C., 5% $CO_2$. Upon reaching subconfluence, Accutase (PAA (Linz, Austria)) was used to collect the cells, and 2 µM of PKH67 (Sigma-Aldrich (St. Louis, Mo.)) was used for labeling according to the product manual. The cells were seeded in the upper wells of a 24-well FluoroBlok plate (Becton Dickinson (Mountain View, Calif.)), at $3\times10^4$-labeled cells/well. After 6 hours of incubation, the medium was exchanged with MessenPro RS medium (DMEM; GIBCO/BRL (Carlsbad, Calif.)) without supplementation. Incubation was continued for 12 hours, and the test substance was added at a concentration of 0.1% to the lower wells of the FluoroBlok. After 8 hours, the lower side of the FluoroBlok membrane was photographed through a microscope equipped with a fluorescence filter, and cells attracted through the membrane were counted using Image J., in a larger fluorescence region than the pore size. The activity of attracting the fat-derived stem cells was evaluated by comparing the fluorescence value in the control wells with the fluorescence value in the test wells.

Figure 5:
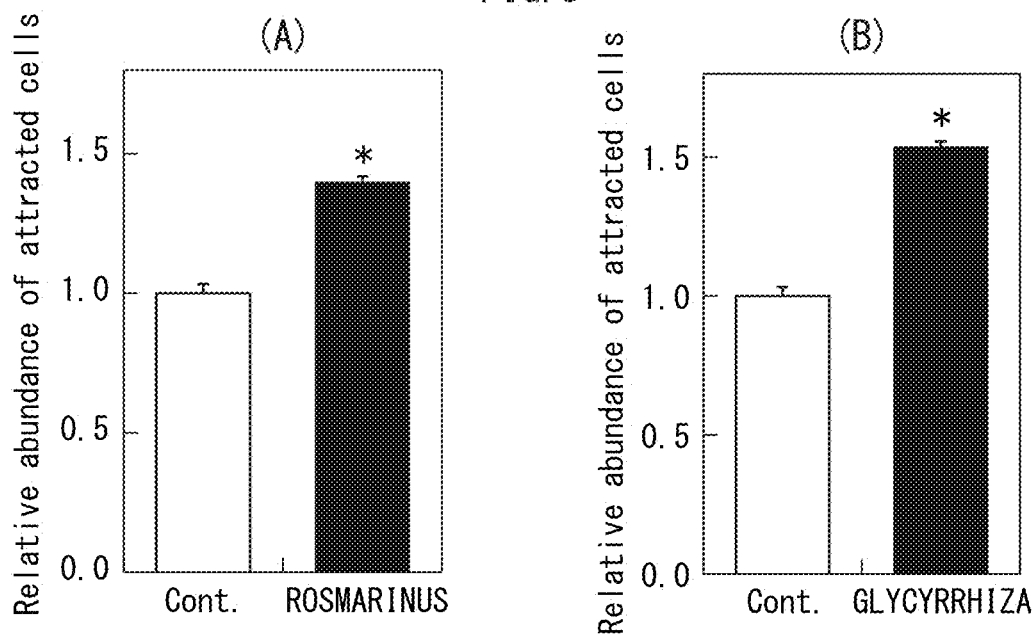
FIG. 5 is a pair of graphs showing attraction of adipose stem cells by rosemary extract (FIG. 5A) and attraction of adipose stem cells by licorice extract (FIG. 5B).

As the test extracts, several cosmetic materials were provided for screening, and among them, rosemary (*Rosmarinus officinalis*) leaf extract (Maruzen Pharmaceuticals Co., Ltd., product code: 6435, extraction solvent: 50% (w/v) butylene glycol) and licorice (*Glycyrrhiza glabra*) root extract (Maruzen Pharmaceuticals Co., Ltd., product code: 9488, extraction solvent: 50% (w/v) butylene glycol) were found to exhibit excellent adipose stem cell attracting activity. The wells to which rosemary extract and licorice extract had been added showed significantly higher fluorescence than the control wells that contained the extraction solvent alone without an extract (Table 1, FIGS. 5A and B, Student's t-test: $P<0.05$). With rosemary extract and licorice extract, the extraction solvent was 50% (w/v) butylene glycol, and this solvent alone was added to the control wells instead of the test extract.

TABLE 2

| Sample name | Fluorescence region (N = 3) | | | Relative value | |
|---|---|---|---|---|---|
| | | | | Mean | S.E.M. |
| Control | 420992 | 511901 | 416364 | 1.00 | 0.03 |
| Rosemary extract | 699476 | 630690 | 555030 | 1.40 | 0.08 |
| Licorice extract | 671535 | 788708 | 610983 | 1.54 | 0.02 |

[Sequence Listing]

What is claimed is:

1. A method for improving skin sagging or aging caused by dermal cavitation in an individual in need thereof, comprising, administering an effective amount of licorice extract or rosemary extract to the individual, wherein the individual suffers from a high degree of dermal cavities, and the effective amount of licorice extract or rosemary extract is effective in attracting adipose stem cells.

2. The method for improving skin sagging or aging according to claim 1, wherein the dermal cavities are filled in with dermal structure derived from adipose stem cells attracted in the dermal cavities by administering an adipose stem cell attractant comprising licorice extract or rosemary extract.

3. The method for improving skin sagging or aging according to claim 2, wherein the dermal structure includes dermal fibroblasts and interstitial components produced by the dermal fibroblasts, due to the attracted adipose stem cells.

4. The method for improving skin sagging or aging according to claim 3, wherein the licorice extract or the rosemary extract permeates through accessory organs.

5. The method for improving skin sagging or aging according to claim 3, wherein the licorice extract or the rosemary extract acts on dermal cavities.

6. The method for improving skin sagging or aging according to claim 2, wherein the licorice extract or the rosemary extract permeates through accessory organs.

7. The method for improving skin sagging or aging according to claim 2, wherein the licorice extract or the rosemary extract acts on dermal cavities.

8. The method for improving skin sagging or aging according to claim 1, wherein the licorice extract or the rosemary extract permeates through accessory organs.

9. The method for improving skin sagging or aging according to claim 1, wherein the licorice extract or the rosemary extract acts on dermal cavities.

10. The method for improving skin sagging or aging according to claim 1, further comprising first determining whether the individual suffers from a high degree of dermal cavities.

11. The method for improving skin sagging or aging according to claim 1, wherein the high degree of dermal cavities corresponds to at least −1.5 mm.

* * * * *